(12) United States Patent
Blattner et al.

(10) Patent No.: US 8,900,849 B2
(45) Date of Patent: Dec. 2, 2014

(54) OXYGEN-REGULATED MICROORGANISMS

(75) Inventors: Frederick R. Blattner, Madison, WI (US); John Walter Campbell, Oak Park, IL (US); Nian Shi, Middleton, WI (US); Buffy Stahl, Oregon, WI (US)

(73) Assignee: Scarab Genomics, LLC, Madison, WI (US)

( * ) Notice: Subject to any disclaimer, the term of this patent is extended or adjusted under 35 U.S.C. 154(b) by 1541 days.

(21) Appl. No.: 12/065,597

(22) PCT Filed: Sep. 8, 2006

(86) PCT No.: PCT/US2006/035200
§ 371 (c)(1),
(2), (4) Date: Aug. 14, 2008

(87) PCT Pub. No.: WO2007/030790
PCT Pub. Date: Mar. 15, 2007

(65) Prior Publication Data
US 2009/0053792 A1  Feb. 26, 2009

Related U.S. Application Data

(60) Provisional application No. 60/715,702, filed on Sep. 8, 2005.

(51) Int. Cl.
| | | |
|---|---|---|
| *C12N 1/20* | (2006.01) | |
| *C12N 15/00* | (2006.01) | |
| *C07H 21/02* | (2006.01) | |
| *C07H 21/04* | (2006.01) | |
| *C07K 1/00* | (2006.01) | |
| *C12N 15/52* | (2006.01) | |
| *C12N 1/00* | (2006.01) | |

(52) U.S. Cl.
CPC . *C12N 1/00* (2013.01); *C12N 15/52* (2013.01)
USPC ............ 435/252.3; 435/252.33; 435/320.1; 530/350; 536/23.1; 536/23.2; 536/24.1

(58) Field of Classification Search
None
See application file for complete search history.

(56) References Cited

PUBLICATIONS

Whisstock et al. Quaterly Reviews of Biophysics, 2003, "Prediction of protein function from protein sequence and structure", 36(3): 307-340.*

Chica et al. Semi-rational approaches to engineering enzyme activity: combining the benefits of directed evolution and rational design, Curr Opin Biotechnol. Aug. 2005;16(4):378-84. Review.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Hirose et al. cDNA cloning and tissue specific expression of a gene for sucrose transporter from rice (*Oryza sativa* L.)., Plant Cell Physiol. Dec. 1997;38(12):1389-96).*
Vlag et al. Quantification of the regulation of glycerol and maltose metabolism by IIAGIc of the phosphoenolpyruvate-dependent glucose phosphotransferase system in *Salmonella typhimurium*., J Bacteriol. Jun. 1994;176(12):3518-26).*
Torres et al. Haem iron-transport system in enterohaemorrhagic *Escherichia coli* O157.H7, Mol Microbiol 23(4):825-833, 1997.*
Shukla et al. Production of D(-)-lactate from sucrose and molasses, Biotechnology Letters (2004), 26: 689-693.*
Matsumura et al. Regulation of *Escherichia coli* superoxide dismutase genes (SODA and SODB) by oxygen, Biotechnology Letters (1993), 15: 229-234.*
International Search Report of PCT/U2006/035200 dated Jan. 15, 2007.
Xu, H., et al., "Postiive and Negative Regulation of Sequences Upstream of the Form II cbb CO-2 Fixation Operon of *Rhodobacter sphaeroides*," Journal of Bacteriology, vol. 176, No. 23, pp. 7299-7308 XP 002411837 , 1994.
Khosla, et al., "Expression of Recombinant Proteins inEscherichia Coli Using an Oxygen-Responsive Promoter," Bio/Technology, vol. 8, pp. 554-558 (1990).
Passoth, et al., "Analysis of the Hypoxia-induced ADH2 Promoter of the Respiratory Yeast *Pichia stipitis* Reveals a New Mechanism for Sensing of Oxygen Limitation in Yeast," Yeast, vol. 20, pp. 39-51, (2003).

\* cited by examiner

*Primary Examiner* — Iqbal H Chowdhury
(74) *Attorney, Agent, or Firm* — Morgan, Lewis & Bockius LLP

(57) ABSTRACT

The present invention relates to novel strains of microorganisms with oxygen-regulated metabolism. The microorganisms have higher growth rates and are more efficient than parental strains. The microorganisms may be used to produce a variety of products of interests, such as recombinant proteins, nucleic acids, such as DNA, amino acids, and chemicals.

9 Claims, 14 Drawing Sheets

WT K12 Superoxide dismutase

Figure 12
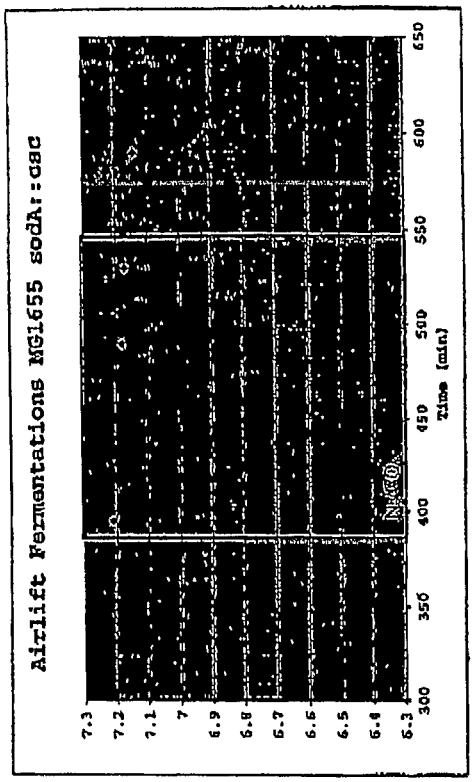
B
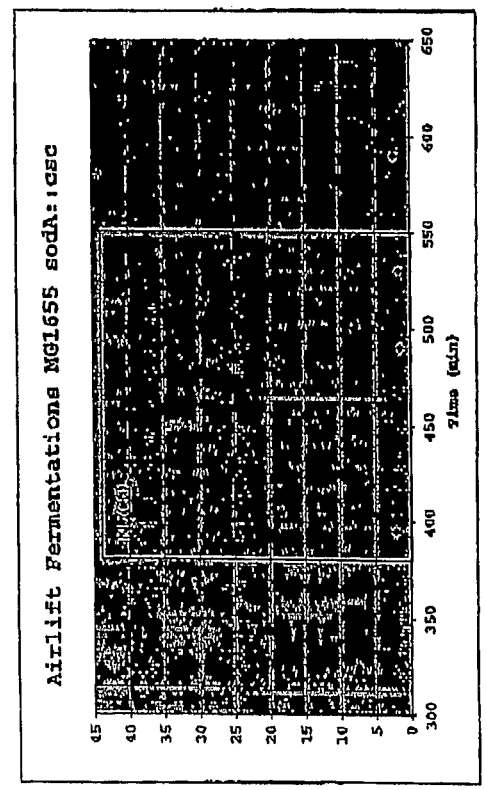
A

SEQUENCE LISTING

```
<160> NUMBER OF SEQ ID NOS: 12

<210> SEQ ID NO 1
<211> LENGTH: 70
<212> TYPE: DNA
<213> ORGANISM: Artificial
<220> FEATURE:
<223> OTHER INFORMATION: Synthetic Primer

<400> SEQUENCE: 1
cccacggagt ggctgtgctg caacatggag cactctggct actgggttaa gtcagatgaa       60
tttaagggaa                                                              70

<210> SEQ ID NO 2
<211> LENGTH: 70
<212> TYPE: DNA
<213> ORGANISM: Artificial
<220> FEATURE:
<223> OTHER INFORMATION: Synthetic Primer

<400> SEQUENCE: 2
caaaaccaca tcaattgaaa cgctgtttta tttttatcgg atcattgttt ctatattgct       60
gaaggtacag                                                              70
```

```
<210> SEQ ID NO 3
<211> LENGTH: 20
<212> TYPE: DNA
<213> ORGANISM: Artificial
<220> FEATURE:
<223> OTHER INFORMATION: Synthetic Primer

<400> SEQUENCE: 3
ttaacccagt agccagagtg                                                    20

<210> SEQ ID NO 4
<211> LENGTH: 70
<212> TYPE: DNA
<213> ORGANISM: Artificial
<220> FEATURE:
<223> OTHER INFORMATION: Synthetic Primer

<400> SEQUENCE: 4
ctgcttacgc ggcattaaca atcggccgcc cgacaatact ggagatgaat atgacgcaat       60
ctcgattgca                                                               70

<210> SEQ ID NO 5
<211> LENGTH: 70
<212> TYPE: DNA
<213> ORGANISM: Artificial
<220> FEATURE:
<223> OTHER INFORMATION: Synthetic Primer

<400> SEQUENCE: 5
caaaaccaca tcaattgaaa cgctgtttta tttttatcgg atcattgttt ttaacccagt       60
agccagagtg                                                               70

<210> SEQ ID NO 6
<211> LENGTH: 24
<212> TYPE: DNA
<213> ORGANISM: Artificial
<220> FEATURE:
<223> OTHER INFORMATION: Synthetic Primer

<400> SEQUENCE: 6
gtaagtcaga tgaatttaag ggaa                                               24

<210> SEQ ID NO 7
<211> LENGTH: 24
<212> TYPE: DNA
<213> ORGANISM: Artificial
<220> FEATURE:
<223> OTHER INFORMATION: Synthetic Primer

<400> SEQUENCE: 7
ctatattgct gaaggtacag gcgt                                               24

<210> SEQ ID NO 8
<211> LENGTH: 26
<212> TYPE: DNA
<213> ORGANISM: Artificial
<220> FEATURE:
<223> OTHER INFORMATION: Synthetic Primer

<400> SEQUENCE: 8
aagaggttta tcactaacat tttgtg                                             26
```

-continued

```
<210> SEQ ID NO 9
<211> LENGTH: 70
<212> TYPE: DNA
<213> ORGANISM: Artificial
<220> FEATURE:
<223> OTHER INFORMATION: Synthetic Primer

<400> SEQUENCE: 9
gcattgtttg ccgatctctt cactgagaaa gaattgcaac agtaattacg ccccgccctg    60
ccactcatcg                                                          70

<210> SEQ ID NO 10
<211> LENGTH: 58
<212> TYPE: DNA
<213> ORGANISM: Artificial
<220> FEATURE:
<223> OTHER INFORMATION: Synthetic Primer

<400> SEQUENCE: 10
acaaacctga attttaagtc cagtacctac gacgcactttt gcgccgaata aatacctg    58

<210> SEQ ID NO 11
<211> LENGTH: 60
<212> TYPE: DNA
<213> ORGANISM: Artificial
<220> FEATURE:
<223> OTHER INFORMATION: Synthetic Primer

<400> SEQUENCE: 11
tgttttggac ttaaaattca ggtcatggat aatgcgtcga ctcctgcaaa accatacccct    60

<210> SEQ ID NO 12
<211> LENGTH: 71
<212> TYPE: DNA
<213> ORGANISM: Artificial
<220> FEATURE:
<223> OTHER INFORMATION: Synthetic Primer

<400> SEQUENCE: 12
gggtgtgcag accgttcgga gcggtaatgg taacttcttg ctggaacata ttcatctcca    60
gtattgtcgg g                                                        71
```

OXYGEN-REGULATED MICROORGANISMS

CROSS REFERENCE TO RELATED APPLICATIONS

This application claims the benefit of U.S. Provisional Application No. 60/715,702, filed Sep. 8, 2005, and International Application PCT/2006/032525 filed Aug. 18, 2006, the contents of which are incorporated herein by reference.

FIELD OF THE INVENTION

The present invention relates to novel strains of microorganisms and fermentation processes involving these microorganisms. More specifically, the present invention relates to genetically modified strains of microorganisms and the use thereof for the production of commercial products, such as recombinant proteins, nucleic acids, amino acids and specialty chemicals. The present invention also relates to methods of preparing strains of microorganisms for such uses.

BACKGROUND

Microorganisms, such as bacteria are used extensively in industrial processes to manufacture biopharmaceuticals, vaccine components, plasmid DNAs, vaccine DNAs and many specialty chemicals, including amino acids. Bacteria used in industrial processes are typically grown in liquid medium supplemented with glucose as a source of carbon. Large amounts of glucose are required in industrial processes to grow bacteria to the high densities desired for maximizing volumetric productivity, for producing specialty chemicals and for maintenance of the bacteria. Bacteria take up and assimilate metabolites at a high rate. The flux of metabolites can be so high that it overwhelms one or more of the biochemical reactions in the central carbon pathways of the bacteria as the concentration of certain metabolites rise. The bacteria dispose of the high concentrations of metabolites by utilizing one or more "overflow" pathways.

*E. coli* tend to secrete acetate when oxygen becomes scarce during high cell density fermentations. The root cause is the need for the cell to dispose of electrons to an acceptor other than $O_2$. The proximate cause is intracellular accumulation of acetyl-CoA, a product of glycolysis, which in the presence of $O_2$ is normally burned by the TCA cycle. However, when $O_2$ is low, the TCA cycle cannot metabolize acetyl-CoA efficiently, so it builds up in the cell. Excess acetyl-CoA is converted to acetate which is excreted along with other organic acids to remove electrons from the cell. This provides a viable but slow metabolic solution for *E. coli* in the wild, but in industrial fermentors as cell density is driven to higher levels, excess acetate can accumulate to toxic levels.

This problem has traditionally been addressed by fed batch fermentation wherein the carbon source is metered into the culture so the cell growth is limited by carbon starvation to levels commensurate with the available $O_2$. Despite metering the carbon source, oxygen utilization eventually becomes limiting at high cell densities. In this situation the fermentor environment also becomes heterogeneous due to the lack of perfect mixing, and the $O_2$ level varies from place to place in pockets. Although acetate excreted in a low $O_2$ region can be taken back up by cells that are carried to regions with more $O_2$, this may be metabolically inefficient and, eventually, as more cells accumulate, the acetate level inexorably climbs even with fed batch technology. As the organic acid levels rise beyond the buffering capacity of the media, pH is maintained by titration with mineral bases such as NaOH which not only require additional equipment and attention from plant personnel, but can also increase the complexity of downstream product purification as well as the salt burden in the fermentor waste stream. A fermentation regimen that increases specific product formation by minimizing over flow metabolism would represent a significant improvement to the art.

SUMMARY OF THE INVENTION

In various embodiments, the present invention provides a microorganism with metabolic flux from a carbon source regulated by oxygen levels. The microorganism may be a prokaryote, such as *E. coli, Shigella, Salmonella, Corynebacter, Lactococcus* or *Streptomycetes*. The microorganism may also be a eukaryote, such as a yeast. The yeast may be *Saccharomyces cerevisiae, Schizosaccharomyces pombe* or *Pichia* species. The carbon source may be glucose, fructose, galactose, mannose, sucrose, maltose, N-acetylglucosamine, β-glucosides, mannitol, cellobiose, sorbose, glucitol or galactitol.

The microorganism may comprise an oxygen-regulated promoter operatively linked to a gene encoding a protein of a phosphoenol pyruvate-dependent phosphotransferase system. The microorganism may comprise an oxygen-regulated promoter operatively linked to a gene encoding a protein of the *E. coli* O157.H7 sucrose metabolism module. The gene operatively linked to the oxygen-regulated promoter may encode a fusion protein. The fusion protein may comprise ubiquitin.

These an other embodiments of the present invention are discussed in further detail herein below,

BRIEF DESCRIPTION OF THE DRAWINGS

FIG. 12 shows the viable cell counts (Panel A) and media pH (Panel B) for MG1655 sodA::csc grown on minimal MOPS media with 0.4% sucrose as the sole carbon and energy source (gray diamonds) and MOPS media with 0.2% glucose and 0.4% sucrose (black squares). The boxed area of the plots indicates the time that the culture was grown under anaerobic conditions.

DETAILED DESCRIPTION OF THE INVENTION

Figure 1:
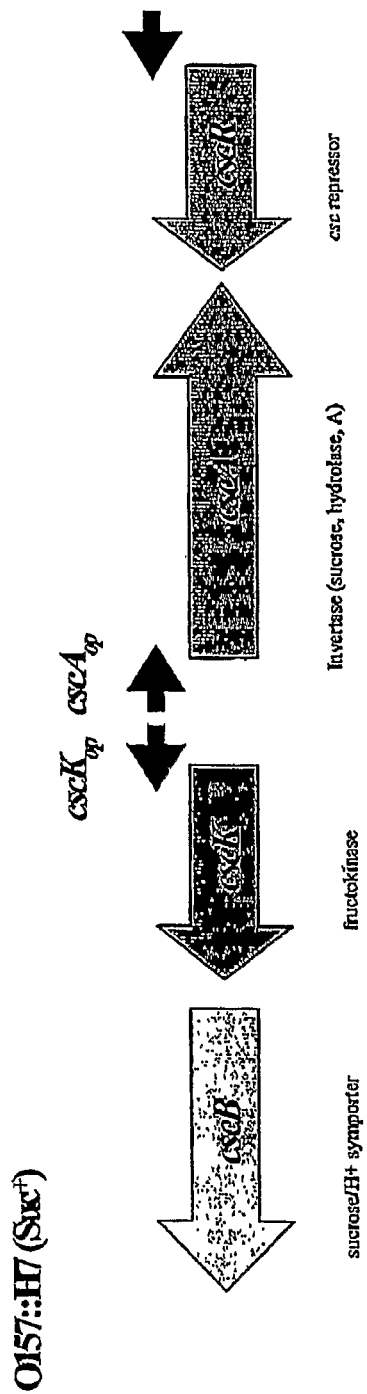
FIG. 1 shows the *E. coli* O157:H7 sucrose metabolism module.

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any way. Embodiments illustrated under any heading may be combined with embodiments illustrated under any other heading.

The use of numerical values in the various ranges specified in this application, unless expressly indicated otherwise, are stated as approximations as though the minimum and maximum values within the stated ranges were both preceded by the word "about." In this manner, slight variations above and below the stated ranges can be used to achieve substantially the same results as values within the ranges. As used herein, the terms "about" and "approximately" when referring to a numerical value shall have their plain and ordinary meanings to one skilled in the pertinent art at issue. Also, the disclosure of ranges is intended as a continuous range including every value between the minimum and maximum values recited as well as any ranges that can be formed thereby. This includes ranges that can be formed that do or do not include a finite upper and/or lower boundary. Accordingly, the skilled person will appreciate that many such ratios, ranges, and ranges of ratios can be unambiguously derived from the data and numbers presented herein and all represent embodiments of the present invention.

In one embodiment, the present invention relates to a microorganism with metabolic flux regulated by oxygen levels. When the microorganism is in an environment with below-threshold levels of oxygen, metabolic flux is reduced. By reducing metabolic flux at low levels of oxygen, overflow metabolism to undesirable metabolites produced in reduced oxygen environments may be reduced. When oxygen levels are increased above a threshold level, metabolic flux may be increased. Within a culture, there may be microenvironments with sufficient oxygen and other microenvironments with insufficient oxygen for efficient product synthesis. The microorganism may be able to self-regulate metabolic flux under varying oxygen levels and thus only consume substrate under conditions that allow efficient product formation.

By regulating the rate of metabolism as a function of oxygen levels, there may be a reduction in the production of acetate and other undesirable over flow metabolites. By allowing the microorganism to self-regulate metabolism, a product of interest may be produced with greater efficiency and less cost.

1. Microorganism

The microorganism may be derived from any parent microorganism. Representative parent microorganisms are available from the American Type Culture Collection. Other representative microorganisms are described in S. Y. Lee, "High Density Culture of Escherichia coli," Tibtech 14:98-103 (1996). The parent organism may be a eukaryote, such as yeast. Representative examples of yeast include, but are not limited to, *S. cerevisiae S. pombe* and *Pichia* species. The parent organism may also be a prokaryote, such as bacteria and may be a chemoheterotrophic organotroph. Representative examples of bacteria include, but are not limited to, *E. coli, Shiigella, Salmonella, Corynebacter, Lactococcus* and *Streptomycetes*.

The microorganism may also be a reduced genome microorganism, such as a reduced genome bacterium. Much of the genetic information contained within the genome of a microorganism may be deleted without detrimentally affecting production of the end metabolite. Moreover, a microorganism with a reduced genome may be advantageous in the production of many products of interest. For example, a reduced genome may lead to the production of fewer native products or lower levels thereof, which may lead to less complex purification of a product of interest. In addition, a microorganism with a reduced genome may be less metabolically demanding and thus may produce a product of interest more efficiently. Reduced genome bacteria are discussed in U.S. Pat. No. 6,989,265, which is incorporated herein by reference. A reduced genome bacteria with limited production of natural periplasmic proteins may be beneficial for expressing recombinant proteins in the periplasm. Examples of suitable reduced genome bacteria strains include, but are not limited to, MDS12, MDS13. MDS39, MDS40, MDS41 MDS42, MDS43, MDS44, MDS45, MDS46, MDS47, MDS48, MDS49, MDS50, MDS51, MDS52, MDS53, MDS54, MDS55, MDS56, MDS57, MDS58, MDS59 and MDS60. The reduced genome microorganism may also be derived de novo from genes and operons from one or more microorganisms.

2. Oxygen-Regulated Metabolic Flux

Oxygen levels may regulate the metabolic flux of a carbon source in a microorganism. The metabolism of a carbon source may be regulated at the importation of the carbon source. For example, the expression of a protein involved in the importation of the carbon source may be placed under the control of an oxygen-regulated promoter.

The metabolism of a carbon source may also be regulated at the first intracellular metabolic step utilizing the carbon source or any metabolic step thereafter, or a combination thereof. For example, the expression of a protein involved in glycolysis or in conversion of the carbon source into a substrate for glycolysis may be placed under the control of an oxygen-regulated promoter.

a. Carbon Source

The carbon source may be any carbon source capable of supporting growth and/or metabolizing of the microorganism, either natively or by introducing heterologous genes or operons encoding enzymes capable of metabolizing the carbon source. The carbon source may be a monosaccharide, such as glucose, fructose, galactose, or mannose. The carbon source may also be a disaccharide, such as sucrose. Other carbon sources include, but are not limited to, maltose, N-acetylglucosamine, β-glucosides, mannitol, cellobiose, sorbose, glucitol and galactitol.

Bacteria may take up a carbon source via the phosphpoenolpyruvate:carbohydrate phosphotransferase (PTS) system. The PTS system may allow rapid and efficient uptake of high-quality exogenous carbon sources and may play a key role in the catabolic regulation of metabolism in many bacteria. Expression of one or more components of the PTS system may be under control of an oxygen-regulated promoter, which may reduce the production of over flow products. An alternative carbon source uptake pathway, regulated by the availability of oxygen may allow more efficient partitioning of substrate into product formation throughout the course of a fermentation.

The PTS system comprises a phospho-relay system in which the EI protein (encoded by ptsH) transfers the phosphate group of phosphoenolpyruvate to the Hpr protein (encoded by ptsI), which in turn phosphorylates a carbohydrate specific EIIA subunit (in *E. coli* the glucose specific EIIA protein is encoded by the crr gene), which can then interact with a membrane associated protein or subunit of the carbohydrate transport complex to internalize and phosphorylate the cognate sugar. The overall reaction converts PEP to pyruvate while transporting an exogenous sugar to an internal sugar-phosphate.

In *E. coli*, the genes encoding the common PTS elements, ptsH and ptsI are associated on the chromosome with the crr gene. All three genes are transcribed from a set of promoters found upstream of ptsH. In addition, an additional promoter or promoter pair within ptsI produces a transcript that includes only ptsI. Expression of some of the promoters upstream of ptsH increases under anaerobic conditions. Increased expression of these genes can result in an increased level of sugar uptake and activation via any of the PTS systems for which a cognate sugar is present. Increased transcription of these genes may therefore play a role in the production of unwanted over-flow metabolites, since as oxygen becomes limiting as an electron acceptor for the TCA cycle, increasing expression of the PTS genes simultaneously increases the capacity for sugar uptake. Replacing the native ptsH-associated promoters with an oxygen-regulated promoter may regulate PTS sugar uptake in an oxygen dependent manner, thus ensuring that consumption of the carbon source is coupled to the presence of oxygen. By controlling expression of the common elements of one or more PTS systems in the cell, the availability and/or utilization of multiple carbon sources may be controlled. As discussed above, uptake and activation of carbon sources can exceed the capacity of the microorganism to efficiently metabolize them, resulting in production of unwanted over flow metabolites. In addition, the production of compounds directly derived from PEP, such as aromatics derived from the shikimic acid pathway, can be limited by consumption of PEP for PTS mediated sugar transport.

1) Sucrose

Sucrose may also be used as a carbon source for the microorganism. Sucrose is a disaccharide of glucose and fructose. In order to be metabolized, sucrose may be transported into the cell and then split into the monosaccharide units. Both glucose and fructose may then enter glycolysis as glucose-6-phosphate and fructose-6-phosphate.

A number of microorganisms, including most strains of *E. coli*, are unable to grow on sucrose. However, some strains have a gene system that allows the uptake and metabolism of sucrose as the sole carbon source. Such gene systems, or portions thereof, may be added to a microorganism to allow the use of sucrose as a carbon source. The genes may be added to the chromosome of the microorganism, or may be added to the microorganism on a plasmid. One or more of the genes added to the microorganism may be placed under the control of an oxygen-regulated promoter. It is also contemplated that gene systems allowing uptake and metabolism of other carbon sources may also be added to the microorganism.

U.S. Pat. Nos. 6,365,723 and 6,855,814, which are incorporated herein by reference, describe a representative example of compact gene system for uptake and metabolism of sucrose that permits the use of sucrose as the sole carbon source. The *E. coli* O157:H7 sucrose metabolism module is shown in FIG. 1. The cscB gene product transports sucrose in to the cell and cscA codes for sucrose hydrolase (invertase), which splits the disaccharide sucrose into fructose and glucose. Gene cscK, codes for fructokinase the first enzyme of glycolytic metabolism of fructose. The cscK gene shows high similarity to other fructokinases and may be redundant to the fruK gene of *E. coli* K-12; however, *E. coli* K-12 cells may lack invertase and sucrose hydrolase activities. The cscR gene product is a repressor that controls expression of the genes of the O157:H7 operon in relation to sucrose availability by binding to the promoters, typical of the lacI-galR family of repressor proteins.

b. Oxygen-Regulated Promoter

Figure 2:
FIG. 2 shows the wild type K12 sodA promoter.

Metabolic flux from the carbon source may be regulated by using oxygen sensitive promoters operative linked to a gene encoding one or more of the proteins involved in metabolism of the carbon source. Representative examples of promoters that are activated in the presence of oxygen are promoters within the cyo operon and superoxide dismutase (sodA), which encodes an enzyme that protects the cell against oxidative damage. The wild type K12 soda chromosomal region is shown in FIG. 2.

By using a positive oxygen sensing promoter, sufficiently high oxygen levels may induce expression of proteins that allow metabolism of the carbon source while minimizing production of over flow metabolites or other by-products. The response time of the promoter may be increased by placing cytoplasmic metabolic proteins under the control of the oxygen sensitive promoter, while non-cytoplasmic proteins (e.g., transmembrane proteins) may be constitutively expressed or placed under control of different promoter. The speed at which metabolism is reduced under diminishing oxygen conditions may be increased by increasing the turnover rate of the metabolic proteins. For example, a protein involved in the metabolism of the carbon source may be expressed as fusion protein with ubiquitin. The invention also encompasses nucleic acid constructs comprising an oxygen regulated promoter operatively linked to a heterologous gene not normally under control of an oxygen sensitive promoter.

c. Growth Rates

The microorganism may have an improved growth rate when grown in the presence of an abundance of a carbon source. When grown in liquid medium comprising from 0% to the maximum tolerated % concentration of a carbon source the microorganism may have a growth rate including, but not limited to, greater than about 25% to about 400% as compared to the parent of the microorganism. The microorganism may be grown in medium comprising a carbon source at a w/v of at least about 0.1%, 0.2%, 0.3%, 0.4%, 0.5%, 0.6%, 0.7%, 0.8%, 0.9%, 1%, 1.5, 2%, 2.5, 3%, 3.5%, 4%, 4.5%, 5%, 5.5%, 6%, 6.5%, 7%, 7.5%, 8%, 8.5%, 9%, 9.5% or 10%. At such conditions, the microorganism may have a growth rate greater than about 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, 200%, 205%, 210%, 215%, 220%, 225%, 230%, 235%, 240%, 245%, 250%, 255%, 260%, 265%, 270%, 275%, 280%, 285%, 290%, 295%, 300%, 305%, 310%, 315%, 320%, 325%, 330%, 335%, 340%, 345%, 350%, 355%, 360%, 365%, 370%, 375%, 380%, 385%, 390%, 395%, or 400% as compared to a parental microorganism.

d. Metabolic Flux

The microorganism may have improved metabolic flux when grown in the presence of an abundance of a carbon source. When grown in liquid medium comprising from 0% to the maximum tolerated % concentration of a carbon source, the microorganism may have a metabolic flux including, but not limited to, from about 5% to about 90% of the carbon source being directed to the desired products. A strain may have a metabolic flux of about 15%, 20%, 25%, 30%, 35%, 40%, 45%, 50%, 55%, 60%, 65%, 70%, 75%, 80%, 85% or 90%.

In general, flux of metabolites through each reaction step in any given pathway depends on the relative rates of the forward reaction and reverse reactions. The flux may refer to the rate of change in concentration of an analyte as a function of time and sample size. The metabolic flux through any single metabolic conversion may be determined using methodologies described in U.S. Pat. Nos. 6,764,817 and 6,849,396, the contents of which are incorporated herein by reference. Further guidance on flux and methods for its determination is provided, for example, by Newsholme, E. A. et al., *Biochem. Soc. Symp.* 43:183-205 (1978); Newsholme, E. A., et al., *Biochem. Soc. Symp.* 41:61-110 (1976); and Newsholme, E. A., and Sart., C., *Regulatioin in Metabolism, Chaps.* 1 and 3, Wiley-Interscience Press (1973), the contents of which are incorporated herein by reference.

e. Production

The microorganisms of the present invention may be able to produce end metabolites or other products of interest at higher rates. When grown in liquid medium comprising from 0% to the maximum tolerated % concentration of a carbon source, the microorganism may produce end metabolites or other products of interest from about 0.001 g/L to about 100 g/L of the carbon source being directed to the desired products. A strain may have a metabolic flux of about 15%, 20%, 25%, 30%, 35%, 40%, 45%, 50%, 55%, 60%, 65%, 70%, 75%, or 80%.

f. Rate of Production

In view of the ability to control the flux of metabolism, the microorganism may produce a variety of amounts of the end metabolite, at a variety of rates, and at variable rates of efficiency of carbon source utilization. The strains of the present invention may produce the end metabolite at least to levels including, but not limited to, about 10 g/L, 20 g/L, 30 g/L, 40 g/L, 50 g/L, 60 g/L, 70 g/L, 80 g/L, 90 g/L, and 100 g/L.

The microorganism may produce the end metabolite at a rate including, but not limited to, at least about 0.50 g/L/hr, 0.75 g/L/hr, 1.00 g/L/hr, 1.25 g/L/hr, 1.50 g/L/hr, 1.75 g/L/hr, 2.00 g/L/hr, 2.25 g/L/hr, 2.50 g/L/hr, 2.75 g/L/hr, 3.00 g/L/hr, 3.25 g/L/hr, 3.50 g/L/hr, 3.75 g/L/hr, 4.00 g/L/hr, 4.25 g/L/hr, 4.50 g/L/hr, 4.75 g/L/hr, and 5.00 g/L/hr.

The microorganism may produce the end metabolite at a rate of efficiency of carbon source utilization including, but not limited to, at least about 5%, 10%, 15%, 20%, 25%, 30%, 35%, 40%, 45%, 50%, 55%, 60%, 65%, 70%, and 75%.

3. Product of Interest

The microorganism may be used to produce a product of interest at high levels of efficiency in media with an abundance of a carbon source. The product of interest produced by the microorganism may be one or more of any products including, but not limited to, chemicals, amino acids, vitamins, cofactors, nucleic acids, such as DNA, fatty acids, growth factors, proteins and intermediates thereof. The product of interest may be a product that is naturally produced by the microorganism. The product of interest may also be a non-natural product that is produced as a result of heterologous genes being added to the microorganism.

The product of interest may be intracellularly located in the microorganism. The product of interest may also be secreted into the periplasm of the microorganism. The periplasm may be beneficial for protein production, because: (i) recombinant human protein may be produced with the correct amino terminus, whereas those produced in the cytoplasm may begin with an additional methionine not present in the natural protein; (ii) many proteins may fold correctly in the periplasmic space (iii) the correct disulfide bonds may be formed in the periplasm; (iv) the periplasmic space may contain much less and far fewer proteins than the cytoplasm, simplifying purification (v) there may be fewer proteases than in the cytoplasm, which may reduce protein digestion and loss; and (vi) expressed proteins may be readily released with other periplasmic proteins by specifically disrupting the outer membrane substantially free of the more abundant cytoplasmic proteins. The product of interest may also be excreted by the cell into the media.

4. Fermentation

The microorganism may be used to produce desired products in batch fermentations, where the entire required amount of the carbon source may be added at the beginning of the fermentation. Not withstanding the ability of the modified cells to tailor carbon source consumption to the availability of oxygen, the strains may also be used to produce desired products in fed batch fermentations. The feeding rate of the carbon source may be any amount up to that which produces the maximum tolerated concentration but is preferably the minimum amount required to maintain maximal growth rate. The strains may also be used to produce desired products in continuous or "chemostat" modes of fermentation, which may allow maintenance of a higher dilution rate.

The microorganism may be used for fermentation processes in a synthetic or natural medium containing at least one carbon source and at least one nitrogen source that may be utilized by the strain by virtue of its possessing the necessary metabolic pathway(s) and, as appropriate, inorganic salts, growth factors and the like.

Illustrative examples of suitable nitrogen sources include, but are not limited to: ammonia, including ammonia gas and aqueous ammonia; ammonium salts of inorganic or organic acids, such as ammonium chloride, ammonium phosphate, ammonium sulfate and ammonium acetate; and other nitrogen-containing substances, including amino acids, meat extract, peptone, molasses, corn steep liquor, casein hydrolysate, soybean cake hydrolysate and yeast extract.

Some amino acids present individually in minimal salts media may not be utilized well by bacteria as carbon sources. Each species of bacterium differs in their ability to utilize each natural amino acid. Amino acids that are not utilized individually may be utilized well in the presence of other amino acids, for instance serine may be used as a carbon source only if glycine, leucine, isoleucine and valine are present. In rich media, such as synthetic amino acid mixes, several amino acids may be utilized preferentially and consumed before other amino acids. Serine, proline, glycine, aspartate, threonine, glutamate and alanine may be completely removed from a mix of the 16 amino acids present in casamino acids, a popular media constituent, while the others are utilized more slowly and incompletely. Similar results are obtained in tryptone broth. If it is desirable to re-utilize amino acids accumulated as end metabolites, then the amino acid may be preferably serine, proline, glycine, aspartate, threonine glutamate of alanine, and the medium may contain the additional amino acids needed to stimulate its use as a carbon source. The medium may also contain a protein hydrolysate including, but not limited to, tryptones, casamino acids and soy hydrolysates.

The present invention has multiple aspects, illustrated by the following non-limiting examples.

Example 1

Oxygen-Regulated Sucrose Uptake and Metabolism

Figure 3:
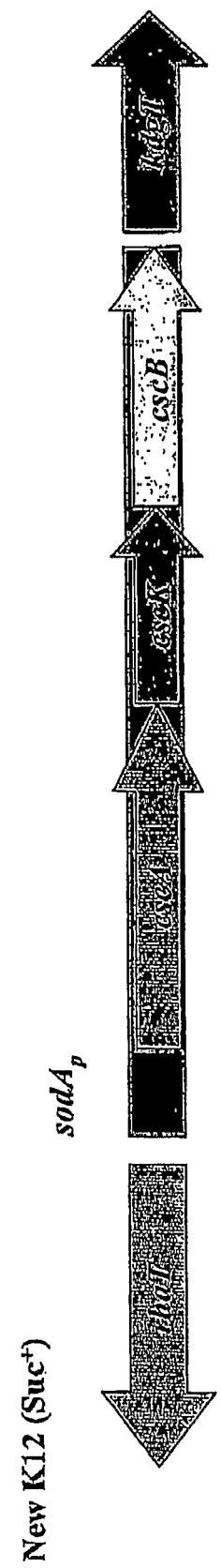
FIG. 3 shows the rearranged O157:H7 sucrose metabolism module controlled by the soda promoter.

A sucrose catabolizing (Suc$^+$) strain of *E. coli* K-12 was produced by replacing the native soda gene with the sucrose metabolism module of *E. coli* O157:H7 as shown in FIG. 3. The genes were rearranged from their original configuration within the module by inverting the cscB gene and placing it in line with cscK. The cscR gene was omitted because the promoter-operator region was replaced by the promoter and regulatory elements of the soda gene. It should be noted that the strain could also have been produced without cscK, since the activity of the gene product is redundant to that of the fruK gene of *E. coli* K-12. The strain could also have been produced by introducing the sucrose metabolism module on a plasmid or into the genome under control of a separate promoter, such as soda.

Figure 4:
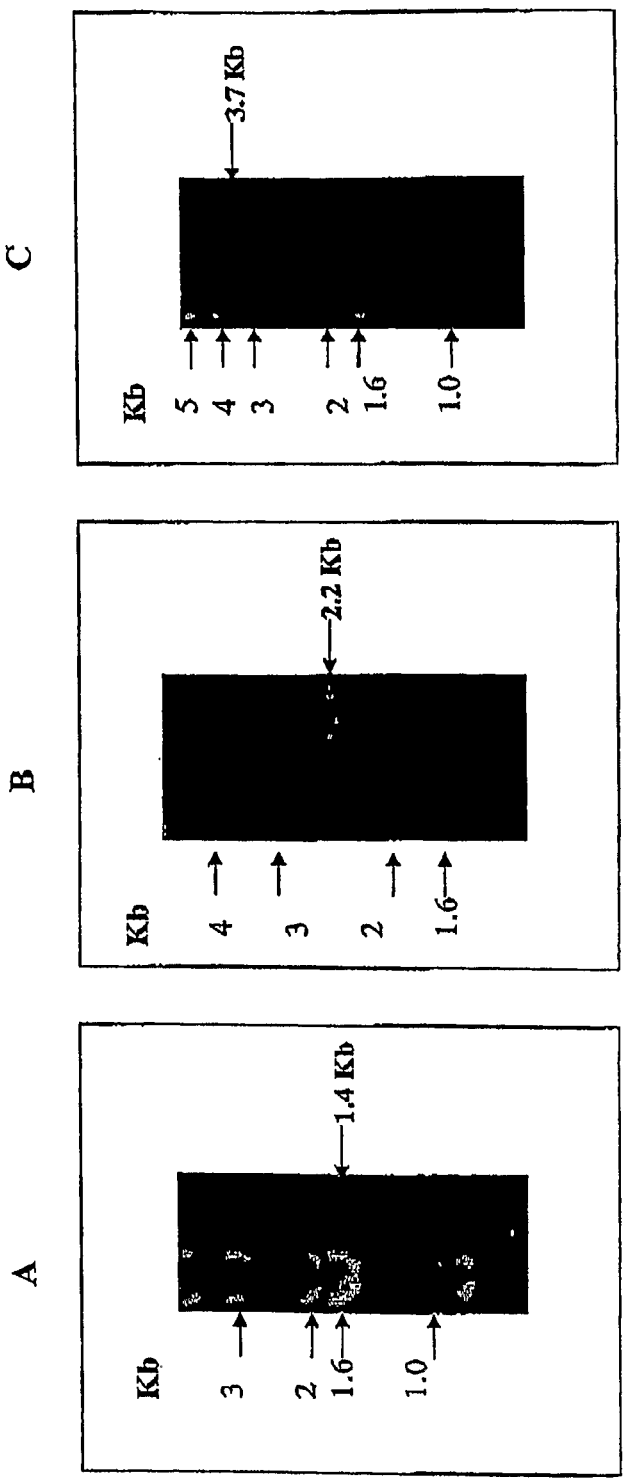
FIG. 4 shows PCR amplification products, a) cscA, b) cscKB, and c) cscA and cscKB recombinant product.

Primers 1 (P1) and 2 (P2) were designed to amplify both cscK and cscB as a single 2.2 Kb piece (FIG. 4*b*). The sequence for P1 was: 5'-CCCACGGAGTGGCTGTGCTGC AACATGGAGCACTCTGGCTACTGGGT-TAAGTCAGATGAATTTAAGGGAA-3' (SEQ ID NO: 1), which has a 50-bp overlap with the 3' end of the cscA gene and 20-bp of the 5' end of the cscK gene including the ribosome binding site (RBS) region of the cscK gene. The sequence for P2 is: 5'-CAAAACCACATCAATTGAAACGCTGTTT-TATTTTTATCGGAT CATTGTTTCTATATTGCTGAAGG-TACAG-3' (SEQ ID NO: 2), which has 50-bp of the 3' end sequence after the soda terminator region and 20-bp of the 3' end of the cscB gene. Primers 3 and 4 were designed to amplify cscA (1.4 kb) (FIG. 4*a*) from O157:H7 genomic DNA. The sequence for P4 is: 5'-CTGCTTACGCGGCAT-TAACAATCGGCCGCCCGACA ATACTGGAGAT-GAATATGACGCAATCTCGATTGCA-3' (SEQ ID NO: 4), which has 50-bp of the soda promoter sequence including the RBS. The sequence for P3 is: 5'-TTAACCCAGTAGCCA-GAGTG-3' (SEQ ID NO: 3), which matches the 3' end sequence of the cscA gene.

In the first round of PCR to amplify cscA or cscKB, a 50 µl PCR reaction was carried out in a tube containing 100 ng O157:H7 genomic DNA, 50 pmol of each primer, 0.2 mM dNTPs and 2.5 U of Pfu polymerase. For the cscA amplification, the reaction went through 1 cycle of 1 min at 95° C., 25 cycles of 1 min of denaturing at 95° C.; 15 sec of annealing at 55° C.; and 4 min extension at 72° C., then a final cycle of 10 min extension at 72° C. For the cscKB amplification, the reaction went through the same cycling as above except the annealing temperature was 48° C.

In the second round of recombinant PCR reactions, an equal molar amount of cscA and cscKB products were mixed as templates in a 50 µl reaction containing 50 pmol of each primer, 0.2 mM dNTPs and 2.5 U of Pfu polymerase. The reaction went through 1 cycle of 5 min at 95° C., 5 cycles of 30 sec of denaturing at 95° C.; 30 sec of annealing at 65° C.; and 7.5 min extension at 72° C., then 25 cycles of 1 min of denaturing at 95° C.; 7.5 min extension at 72° C. and a final cycle of 10 min extension at 72° C. The resultant product was the expected size of 3.7 kb (FIG. 4*c*).

Figure 5:
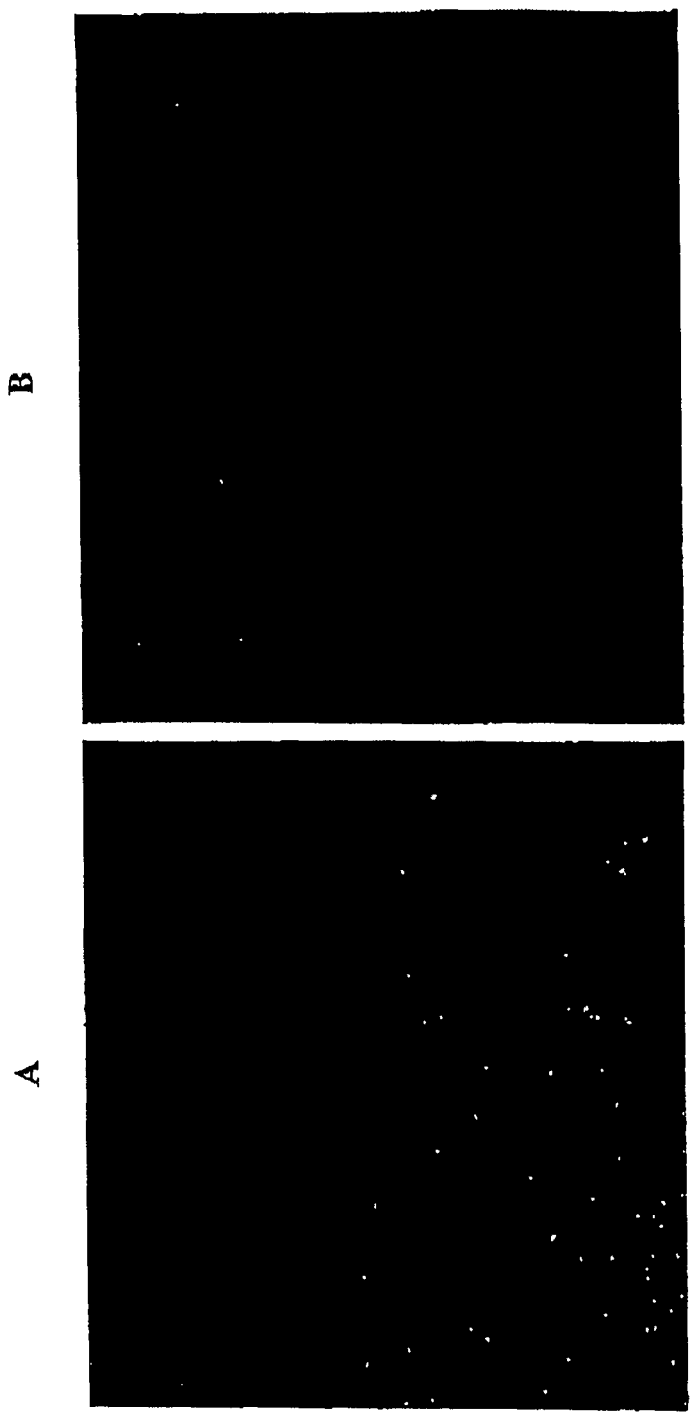
FIG. 5 shows (a) MG1655 cells grown on M9 medium-containing 1% sucrose as the sole carbon source with no colony formation, and (b) MG1655 soda pKD46 containing the cscAKB operon wherein recombinants were able to grow on M9 medium plus 1% sucrose.

The recombinant PCR products contained 50-bp of soda 5' sequence, cscA, cscK, cscB, and 50 bp of the 3' end sequence after the soda terminator. Thus, the cscAKB operon from O157:H7 was placed under control of the soda promoter of MG1655, to produce MG1655 sodA:csc. The PCR products were purified and used for electroporation of the sodA::Tn5 mutant of MG1655, containing plasmid pKD46. MG1655 cells cannot grow on M9 medium containing 1% sucrose as the sole carbon source, as shown in FIG. 5*a*. The transformed cells containing the cscAKB operon, however, were able to grow on the same medium after 2 days at 30° C. in the presence of ampicillin (100 µg/ml final concentration) as shown in FIG. 5B.

Example 2

Oxygen-Regulated Sucrose Metabolism

Figure 6:
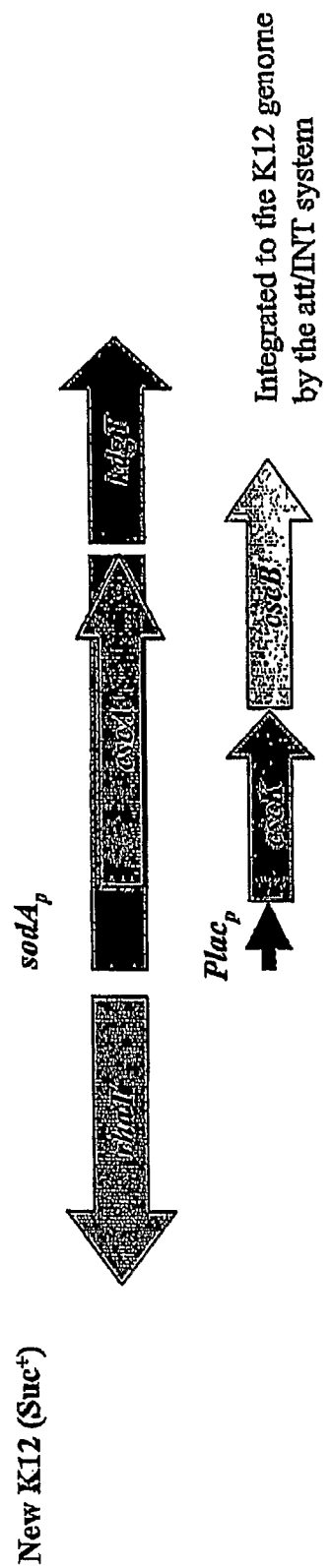
FIG. 6 shows an alternate embodiment of the invention wherein only cscA is controlled by oxygen by the soda promoter and a separate operon ($Plac_p$) controls cscKB.

Invertase may be the bottleneck through which sucrose metabolism must flow. As a cytoplasmic enzyme, invertase can turn over more quickly than a membrane protein. This is important in achieving a rapid shutdown of function. In fact, the rate of its degradation can be speeded up if necessary by ubiquitin tags and other such modifications. By contrast, levels of cscB are is unlikely to be quickly regulated since the symporter is a membrane protein. As a result, we produced the Suc$^+$ strain shown in FIG. 6. The construct provides a separate operon for independently controlling the sucrose symporter cscB using a lac promoter. As before, the fructokinase gene (cscK) may be superfluous.

Figure 7:
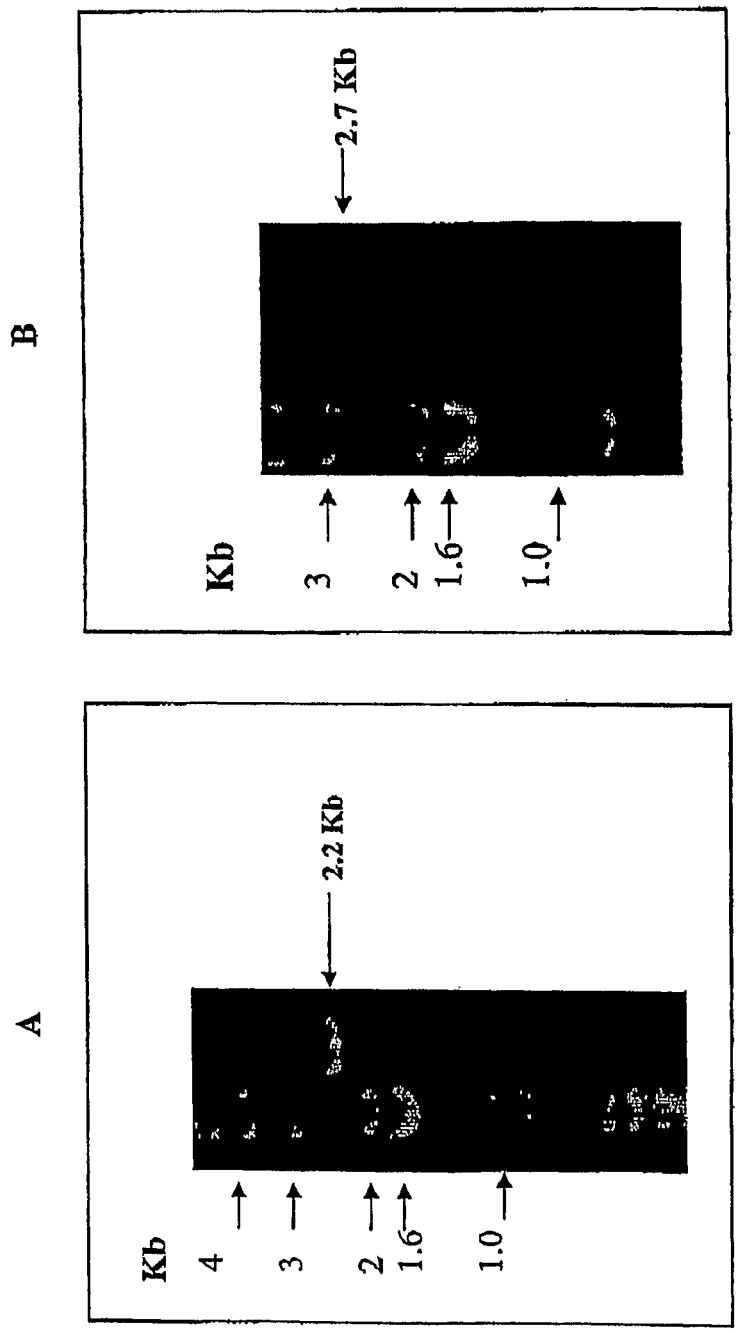
FIG. 7 shows PCR amplification products, a) cscKB, and b) $Plac_{op}$-cscKB-terminator fragment

Primers 4 and 5 were designed to amplify cscA (1.4 kb) from O157:H7 genomic DNA. P4 was the same primer described in Example 1. The sequence for P5 is: 5'-CAAAACCACATCAATTGAAACGCTGTTT-TATTTTTATCGGATCATTGTTTTTAA CCCAGTAGC-CAGAGTG-3' (SEQ ID NO: 5). Thus, the cscA gene is flanked by 50-bp of 5' and 3' sequences of sodA (sodAp-cscA-sodAt). Primers K5 and B3 were designed to amplify both cscK and cscB in one piece (2.2 Kb) (FIG. 7*a*). The sequence for K5 is: 5'-GTAAGTCAGATGAATTTAAGG-GAA-3' (SEQ ID NO: 6), which includes the RBS region of the cscK gene. The sequence for B3 is: 5'-CTATATTGCT-GAAGGTACAGGCG T-3' (SEQ ID NO: 7), which has 20-bp of the 3' end of the cscB gene.

PCR was carried out to amplify cscA or cscKB. A 50-ml PCR reaction was carried out in a tube containing 100 ng O157 genomic DNA, 50 pmol of each primer, 0.2 mM dNTPs and 2.5 U of Pfu polymerase. The reaction went through 1 cycle of 1 min at 95° C., 25 cycles of 1 min of denaturing at 95° C.; 15 sec of annealing at 55° C.; and 4 min extension at 72° C., then a final cycle of 10 min extension at 72° C.

Four microliters of the cscKB product was cloned into a pCR-Blunt vector (Invitrogen) at the EcoRI site to create pFD1. Thus, cscKB product is placed under the control of an inducible Plac promoter. The 2.7-kb Plac-cscKB-terminator fragment was excised from the plasmid by PvuII digestion and gel-purified (FIG. 7*b*). This fragment was sub-cloned into the SzaI site of pJW23, which contains an att site. The new plasmid, named pFD6, was then digested with NotI, and the larger fragment recovered after gel purification. This fragment, containing the Plac-cscKB-terminator was re-ligated to generate pFD7. Plasmids pFD7 and pJW289 were co-transformed into a sodA::Tn5 mutant of MG1655 or MDS42 (without pKD46) to enable integration. The pJW289 plasmid was cured later as described previously. The pKD46 plasmid was introduced back to the cured host for recombination.

The PCR product of sodAp-cscA-sodA, was then used to transform the new host to enable recombination. The transformed cells were plated on M9 medium containing 1% sucrose as a sole carbon source. Transformants able to grow on the medium have a Suc+ phenotype.

Example 3

Figure 8:
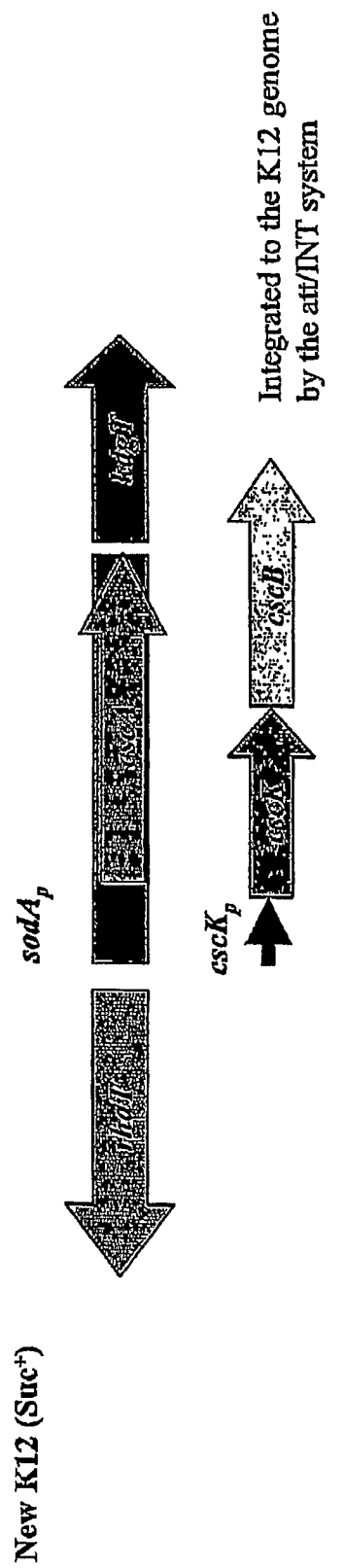
FIG. 8 shows an alternate embodiment of the invention wherein only cscA is controlled by oxygen by the soda promoter and a separate operon ($cscK_p$) controls cscKB.

Control of Sucrose Metabolism by an Oxygen-Sensitive Promoter and Sucrose Uptake by a Sucrose Repressor for Sucrose Positive Bacteria The third example preserves the sucrose repressor CscR to control the level of sucrose in the cell in a normal fashion for sucrose positive strains such as O157:H7. This scheme is tantamount to transplanting the cscA gene from the normal position in the sucrose operon of O157:H7 into the sodA operon. This method of control may be the most effective in regulating acetate because the pool of sucrose will be fixed and the only controlling function is the level of invertase, the bottleneck enzyme. The cscR gene is eliminated from this scheme, which results in constitutive transport of sucrose and fructokinase activities. As before, the sodA gene may either be replaced by cscA or combined in series with cscA as shown in FIG. 8.

Primers 4 and 5 were designed to amplify cscA (1.4 kb) from O157 genomic DNA. P4 and P5 were described in Example 1. Thus, the cscA gene is flanked by 50-bp of 5' and 3' sequences of sodA. Primers ProK5 and B3 were designed to amplify both cscK and cscB in one piece (2.2 Kb). The sequence for ProK5 is: 5'-AAGAGGTTTATCACTAA-CATTTTG TG-3' (SEQ ID NO: 8), which includes the entire promoter region of the cscK gene. The sequence for B3 was the same as described before.

Figure 9:
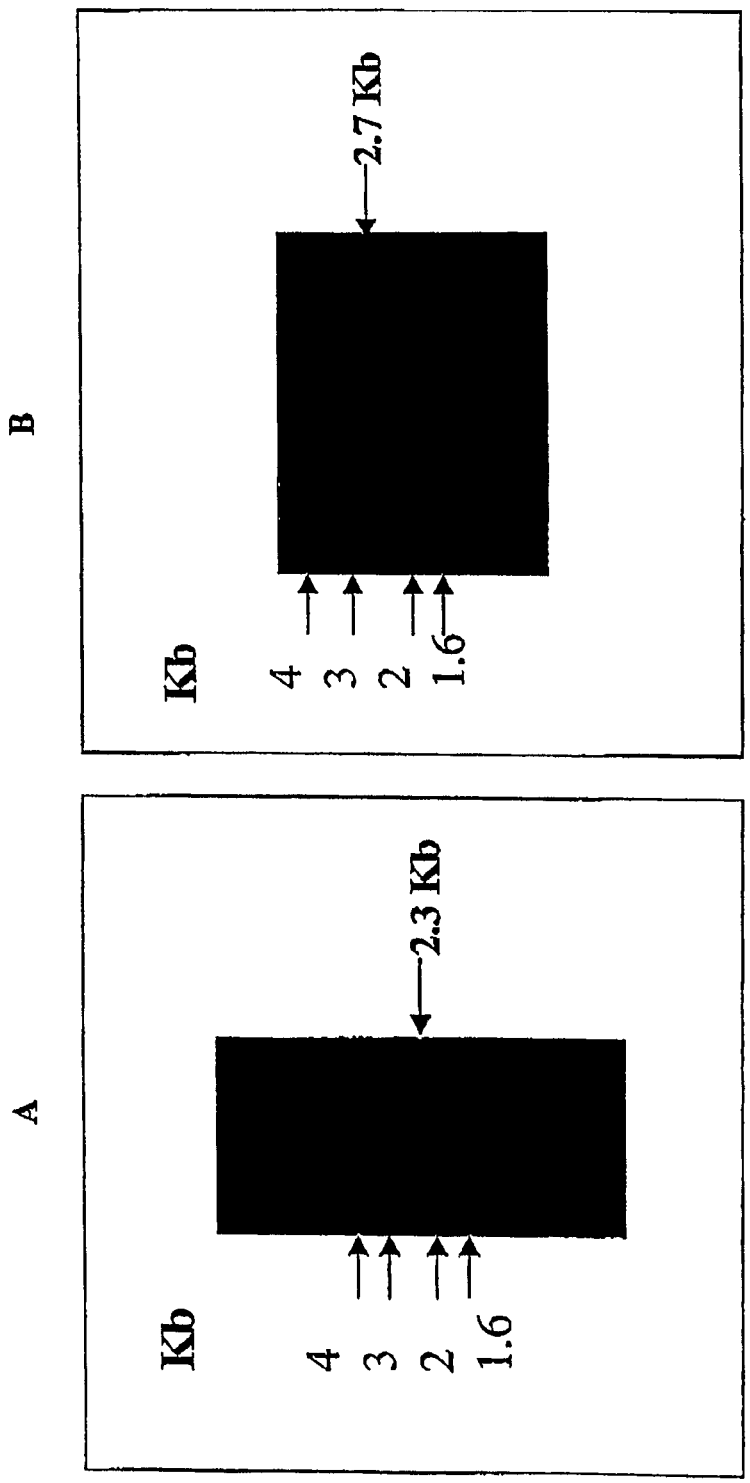
FIG. 9 shows PCR amplification products, a) cscProK-B, and b) cscProK-B fragment cut as a HindIII-XbaI fragment.

PCR was carried out to amplify cscProK-B (2.3 kb) (FIG. 9a). A 50-µl PCR reaction was carried out in a tube containing 100 ng O157 genomic DNA, 50 pmol of each primer, 0.2 mM dNTPs and 2.5 U of Pfu polymerase. The reaction went through 1 cycle of 1 min at 95° C., 25 cycles of 1 min of denaturing at 95° C.; 15 sec of annealing at 55° C.; and 4 min extension at 72° C., then a final cycle of 30 min extension at 72° C.

Four microliters of the cscProK-B product was cloned into a pCR-Blunt vector (Invitrogen) to create pFD8. The cscProK-B fragment was cut out as a HindIII-XbaI fragment (2.7 kb) (FIG. 9b) and sub-cloned into pJW23, which contains an att site. The new plasmid pFD14 was then cut with NotI, and the larger fragment recovered after gel purification. This fragment, containing the cscProK-B-terminator was re-ligated to produce pFD15. Plasmids pFD15 and pJW289 were co-transformed into a sodA::Tn5 mutant of MG1655 or MDS42 (without pKD46) to enable integration. Both plasmids were later cured as described previously. Plasmid pKD46 was then introduced back into the cured host.

The PCR products of cscA were then used to transform the above new hosts to enable recombination. The transformed cells were plated on M9 medium containing 1% sucrose as a sole carbon source. Transformants able to grow on the medium have a Suc+ phenotype.

Example 4

Oxygen-Regulated Growth of Sucrose Metabolism

Aerobic dependent growth of the MG1655 sodA::csc strain of Example 1 was examined using sucrose as a sole carbon and energy source and monitoring growth throughout an aerobic-anaerobic-aerobic cycle. The cycle was initiated by switching the fermentor from air to a 95:5 mixture of Nitrogen and carbon dioxide, and then back to air after a suitable interval in 500 ml air-lift fermentations.

Figure 10:
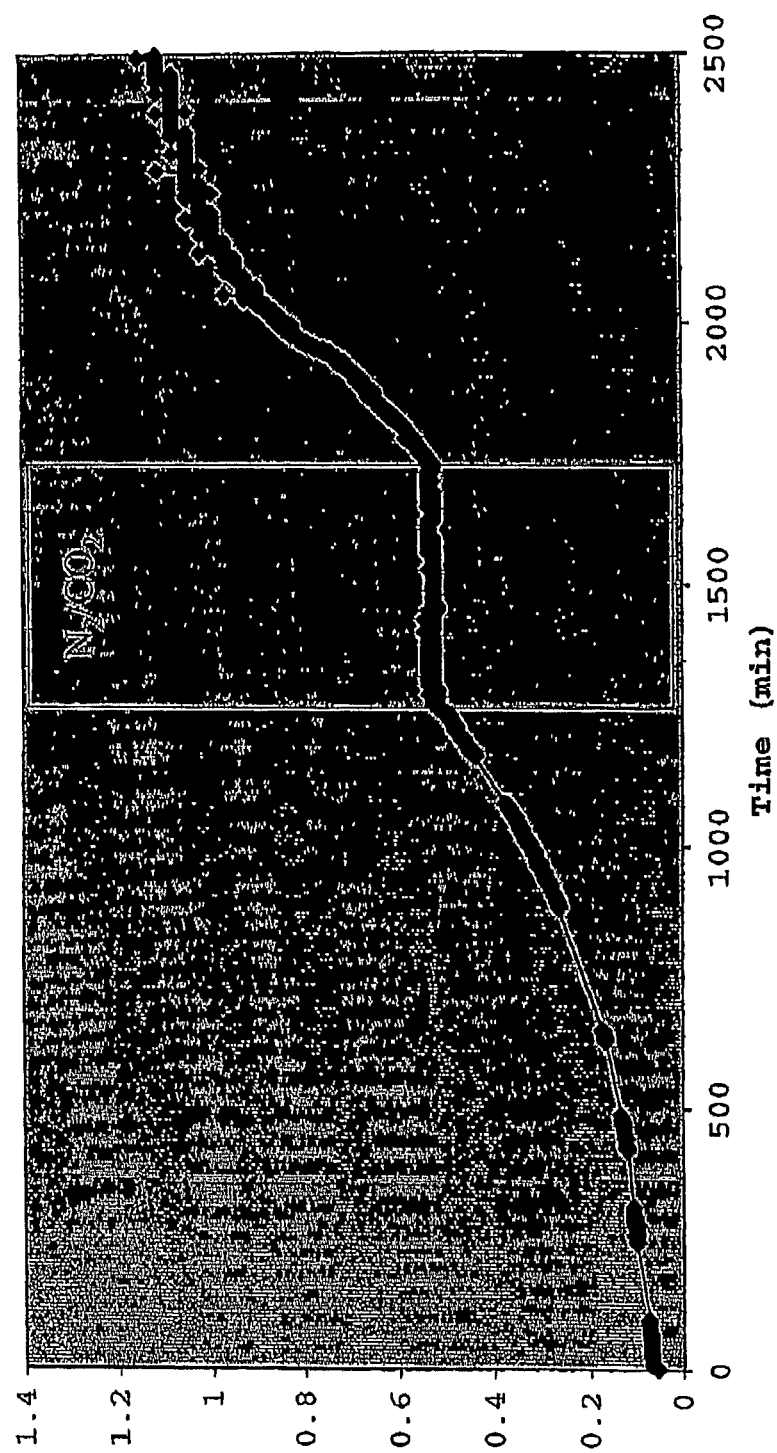
FIG. 10 shows the growth curve of MG1655 sodA::csc on minimal MOPS media with 1% sucrose. The boxed area of the curve indicates the time that the culture was grown under anaerobic conditions.

FIG. 10 represents a typical growth curve of the strain on minimal MOPS media with 1% sucrose as the sole carbon and energy source. The lack of growth under anaerobic conditions indicates the cells were no longer able to catabolize sucrose. In contrast, growth of MG1655 sodA::csc on glucose plus sucrose is relatively unchanged by changes in head space gas, since glucose transport and glycolysis are not solely affected by the aerobic or anaerobic status of the culture.

Figure 11:
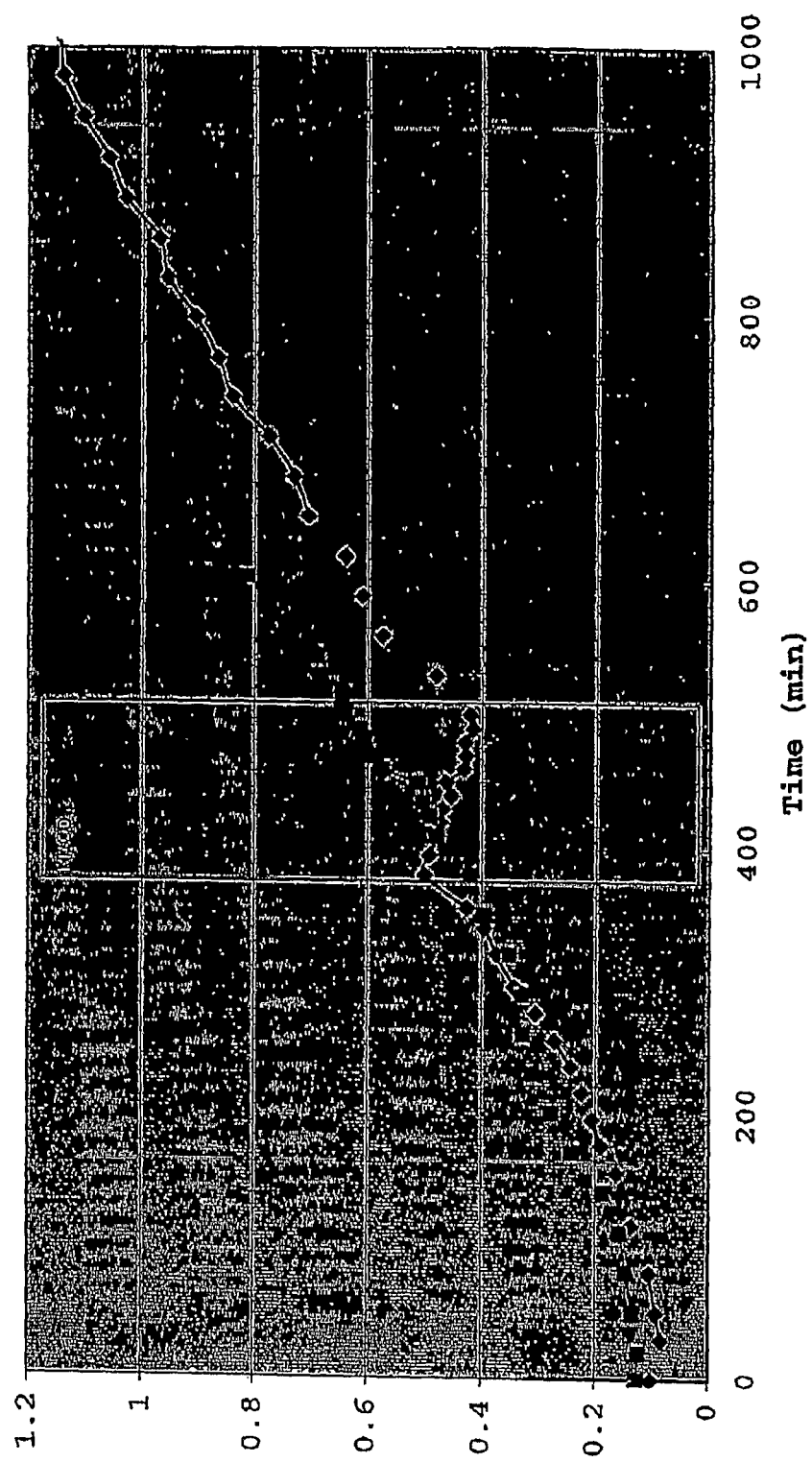
FIG. 11 shows the growth curve of MG1655 sodA::csc on minimal MOPS media with 0.4% sucrose as the sole carbon and energy source (gray diamonds) and MOPS media with 0.2% glucose and 0.4% sucrose (black squares). The boxed area of the curve indicates the time that the culture was grown under anaerobic conditions.

FIG. 11 depicts the results of two similar air lift fermentations, one carried out in minimal MOPS media containing 0.4% sucrose as the sole carbon and energy source and one carried out in the same media supplemented with 0.2% glucose, in addition to 0.4% sucrose as a carbon and energy source. The strain did not grow on sucrose under anaerobic conditions, but continued to catabolize glucose whether oxygen was present or not. In addition to the growth plots shown in FIGS. 10 and 11 are confirmed by the observation that the overall viable cell counts did not change throughout the anaerobic phase in the sucrose only culture, while they continued to increase when exogenous glucose was present (shown in FIG. 12A). This indicates that there is no biochemical restriction on glycolysis and that glucose produced from sucrose (by the action of the csc gene products) could support anaerobic growth if it occurred. Lack of growth on sucrose under anaerobic conditions is therefore due to lack of transcription of the csc genes from the oxygen-dependent soda promoter.

In addition, the pH profiles (FIG. 122B) demonstrate that growth on sucrose generates very little acid, whereas the culture containing both sucrose and glucose produces a large amount of acid. This also supports the notion that little or no sucrose catabolism takes place during the anaerobic phase of the fermentation since anaerobic assimilation of glucose is known to generate large amounts of acetate and formate. The inability of the culture growing on sucrose to produce any acid during the course of the anaerobic shift indicates that little or no glucose is available within the cell in the absence of oxygen.

Example 5

Control of PTS Carbohydrate System by an Oxygen-Sensitive Promoter

Figure 13:
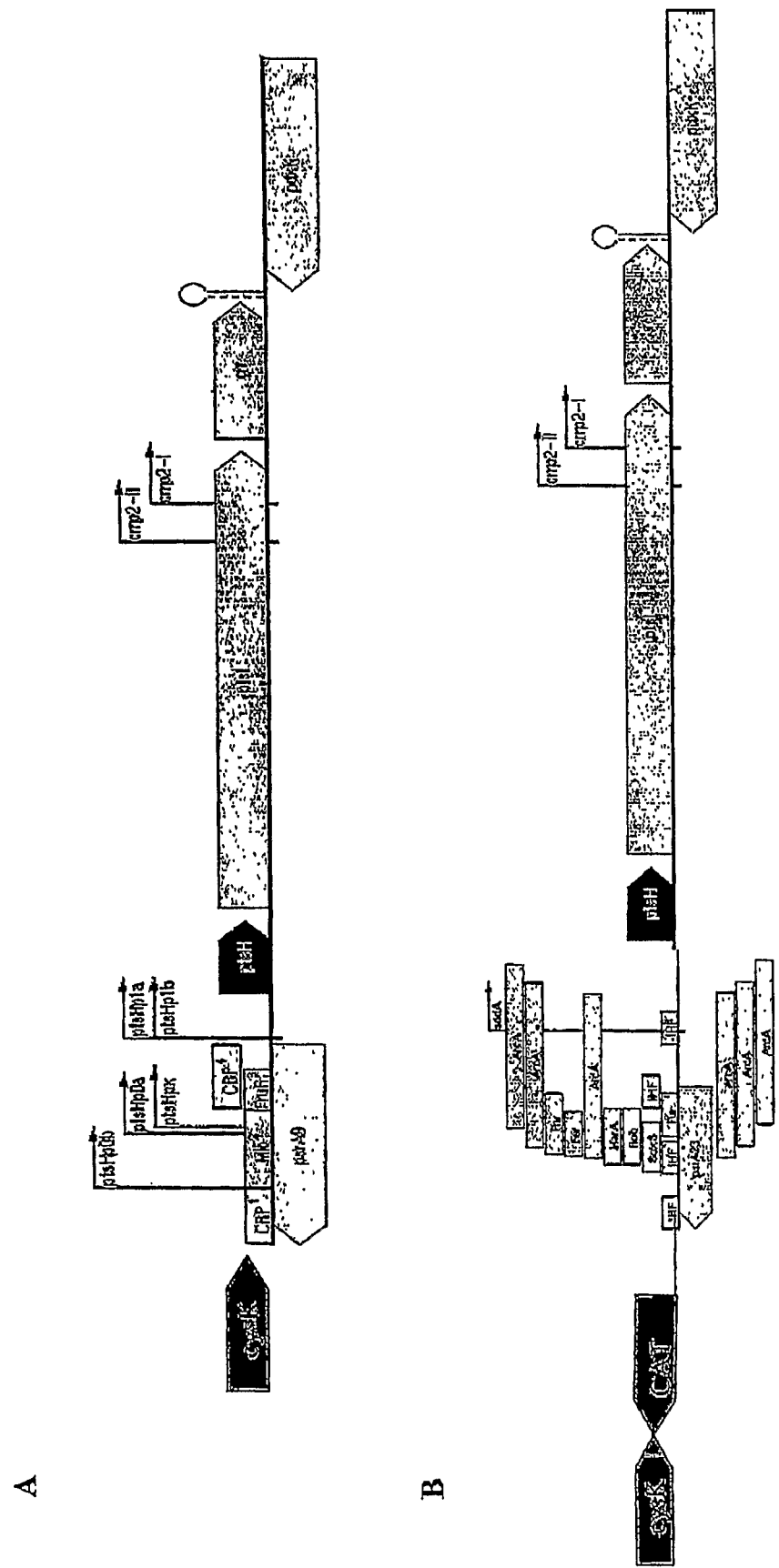
FIG. 13 illustrates the replacement of native PTS promoters with the soda promoter.
Figure 14:
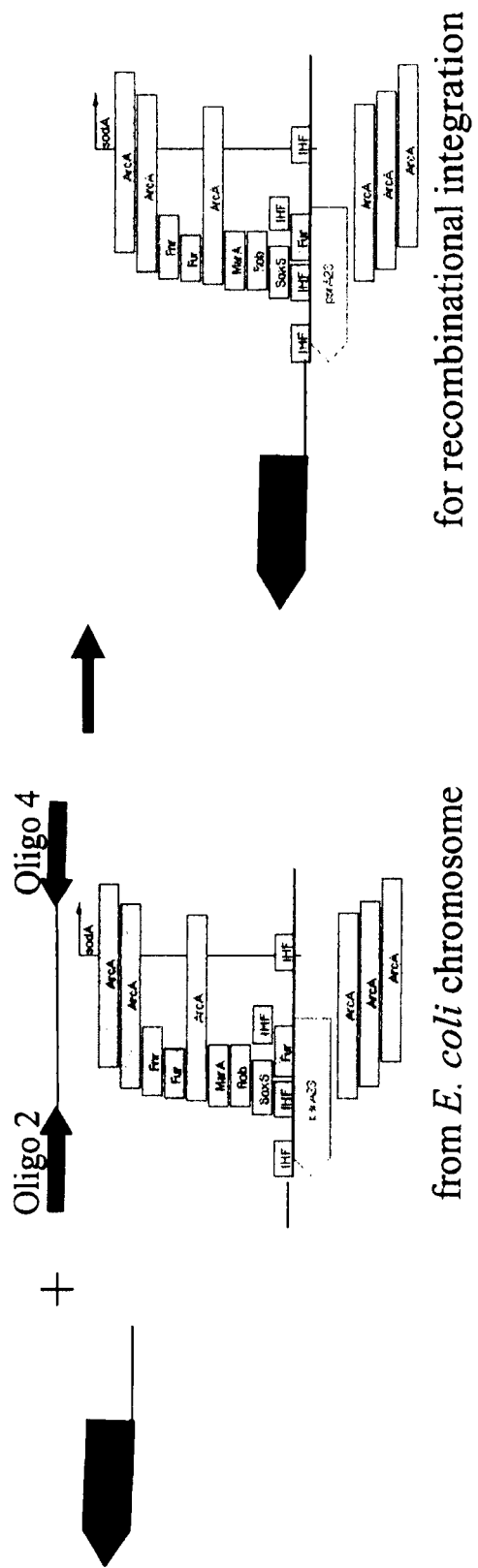
FIG. 14 illustrates the strategy for recombinant construction of PTS regulated by the soda promoter and the oligonucleotides that may be used for PCR amplification.

Replacement of the native PTS promoters with the sodA promoter is illustrated in FIGS. 13 and 14. The desired construct is produced in three steps. The first step involves the production of two separate PCR products sharing a unique sequence homologous to their chromosomal targets at one end, as well as a common sequence to allow fusion of the two PCR products at the opposite ends. The first of the initial PCR products includes 45 bases of sequence homologous to the 3' end of the cysK gene, the complete chloramphenicol acetyltransferase gene (CAT) plus it's promoter as well as a non-coding linker sequence to provide homology to the second PCR product (described below). The CAT gene is amplified from plasmid pACYC 184 using a primer designated as Oligo 1 with the sequence 5'-gcattgtttg ccgatctcttcactgagaaagaattg-caacagtaaTTACGCCCCGCCCTGCC ACTCATCG-3' (SEQ ID NO: 9), where the lower case sequence is homologous to the 3' end of eysK and the upper case sequence is homologous to the 3'-end of the CAT gene. The second oligo in this PCR reaction is designated Oligo 3 with the sequence 5'-acaaacct-gaatttt aagtccagtacctaCGACG-CACTTTGCGCCGAATAAATACCTG-3' (SEQ ID NO: 10), where the lower case sequence is the non-coding sequence homologous with the second PCR product and the upper case sequence is homologous to the 5'-end of the CAT promoter region. A 50-μl PCR reaction is carried out in a tube containing 1 ng pACYC184 DNA, 50 pmol of each primer, 0.2 mM dNTPs and 2.5 U of Pfu polymerase. The reaction went through 1 cycle of 1 min at 95° C., 30 cycles of 1 min of denaturing at 95° C.; 15 sec of annealing at 55° C.; and 2 min extension at 72° C., then a final cycle of 10 min extension at 72° C.

The second of the initial PCR products includes a short non-coding sequence to provide homology to the first PCR product, the intact oxygen-dependent sodA promoter and 45 bases of sequence homologous to the 5' end of the ptsH gene. The sodA promoter region is amplified from E. coli chromosomal DNA using a primer designated as Oligo 2 with the sequence 5'-tgttttggacttaaaattcaggtcatg-gatAATGCGTCGACTCCTGCAAAACCATACCC T-3' (SEQ ID NO. 11), where the lower case sequence is the non-coding sequence homologous with the first PCR product and the upper case sequence is homologous to the 5'-side of the soda promoter region of the E. coli chromosome. The second oligo of this PCR reaction is designated Oligo 4 with the sequence 5'-gggtgtgcagaccgttcggagcggtaatggtaacttcttg ctggaaCATATTCATCTCCAGTATTGTCGGG-3' (SEQ ID NO: 12), the lower case sequence is homologous to the 5'-end of ptsH and the upper case sequence is homologous to the 3'-side of the soda promoter. This oligo effectively replaces the start codon of soda with the start codon of ptsH. A 50-μl PCR reaction is carried out in a tube containing 100 ng E. coliMG1655 DNA, 50 pmol of each primer, 0.2 mM dNTPs and 2.5 U of Turbo Pfu. The reaction went through 1 cycle of 2 min at 95° C., 30 cycles of 1 min of denaturing at 95° C.; 15 sec of annealing at 55° C.; and 1 min extension at 72° C., then a final cycle of 5 min extension at 72° C.

The PCR products of each reaction are recovered from agarose gels and purified on Qiagen purification columns prior to a second round of PCR. In this reaction the two first round PCR products are denatured and allowed to re-anneal prior to extension. A 50-111 PCR reaction was carried out in a tube containing 5 ng of each purified, first round PCR product, 0.2 mM dNTPs and 2.5 U of Pfu polymerase. The reaction goes through 1 cycle of 2 min at 95° C., 10 cycles of 1 min of denaturing at 95° C.; 15 see of annealing at 55° C.; and 1 min extension at 72° C. After the first 5 cycles 50 pmoles of Oligo 1 and Oligo 4 are added to the reactions and the reactions are continued for an additional 25 cycles, followed by a final cycle of 5 min extension at 72° C. The second round PCR product is purified using a Qiagen column and transformed into MG1655 or MDS42 containing pKD46 to enable integration. Stable integrants are isolated as chloramphenicol resistant colonies. The pKD46 plasmid is cured as described previously.

Example 6

Oxygen-Regulated Growth of Sugar Metabolism

Transcriptional regulation of the PTS carbohydrate transport system from oxygen regulated promoters reduces the role the PTS system plays in sugar consumption under anaerobic conditions. Although glucose or other carbohydrates can still be taken up via non-PTS systems rates of assimilation are greatly reduced since the PTS system represents the highest velocity sugar uptake strategy in E. coli. An additional benefit of bringing expression of the ptsH and ptsI genes, which play a common role in all PTS systems in E. coli, under the control of an oxygen regulated promoter allows a single point of regulation to control consumption of all PTS sugars. By direct analogy with the sucrose model described in earlier examples, growth of E. coli strains on other sugars can be constrained to more closely match the availability of oxygen as a terminal electron acceptor thereby minimizing production of over flow metabolites by the engineered cell for a broad range of PTS sugars.

The invention claimed is:

1. An *E. coli* comprising an oxygen-regulated promoter selected from the group consisting of a cytochrome o oxidase (cyo) promoter and a superoxide dismutase (sodA) promoter operatively linked to a sequence selected from the group consisting of a sequence comprising the cscA gene of the *E. coli* O157.H7 chromosomally-encoded sucrose catabolism (csc) module and a sequence comprising the ptsH, ptsI and carbohydrate repression resistant (crr) genes of the *E. coli* phosphoenol pyruvate-dependent phosphotransferase system (pts) wherein metabolic flux from a carbon source in the *E. coli* is decreased in response to a reduction in oxygen levels and wherein the *E. coli* is sucrose catabolizing (Suc+) when said oxygen-regulated promoter is operatively linked to said sequence comprising the cscA gene.

2. The *E. coli* of claim 1 wherein said oxygen-regulated promoter is operatively linked to a sequence comprising the ptsH, ptsI and crr genes of the *E. coli* phosphoenol pyruvate-dependent phosphotransferase system.

3. The *E. coli* of claim 1 wherein said oxygen-regulated promoter is operatively linked to a sequence comprising the cscA gene of the *E. coli* O157.H7 chromosomally-encoded sucrose catabolism module.

4. The *E. coli* of claim 2 wherein one or more of the genes encodes a fusion protein comprising a protein of the *E. coli* phosphoenol pyruvate-dependent phosphotransferase system and ubiquitin.

5. The *E. coli* of claim 3 wherein the gene encodes a fusion protein comprising the protein of the *E. coli* O157.H7 chromosomally-encoded sucrose catabolism module and ubiquitin.

6. The *E. coli* of claim 3 wherein said sequence further comprises the cscK and cscB genes of the *E. coli* O157.H7 chromosomally-encoded sucrose catabolism (csc) module.

7. The *E. coli* of claim 3 wherein the cscK and cscB genes of the *E. coli* O157.H7 chromosomally-encoded sucrose catabolism (csc) module are not operatively linked to an oxygen regulated promoter.

8. A method for regulating metabolic flux in a microorganism comprising culturing the *E. coli* of claim 1 under suitable nutrient conditions and oxygen concentrations to produce a desired metabolic flux.

9. A method for reducing the production of overflow metabolites in microorganism the method comprising culturing the *E. coli* of claim 1 under nutrient conditions and under oxygen concentrations below, above, or at a threshold level of oxygen thereby altering the flow of carbon through one or more metabolic pathway that produces said overflow metabolites.

* * * * *